United States Patent [19]

Fromm et al.

[11] 4,387,224

[45] Jun. 7, 1983

[54] MELAMINE QUALITY BY REACTIVATION OF THE MELAMINE SYNTHESIS CATALYST

[75] Inventors: Dieter Fromm, Gruenstadt; Ernst-Juergen Schier, Altleiningen; Hans H. Schneehage, Weisenheim; Wolfgang Vodrazka, Freinsheim, all of Fed. Rep. of Germany

[73] Assignee: BASF Aktiengesellschaft, Fed. Rep. of Germany

[21] Appl. No.: 420,484

[22] Filed: Sep. 20, 1982

[30] Foreign Application Priority Data

Sep. 26, 1981 [DE] Fed. Rep. of Germany ....... 3138419

[51] Int. Cl.³ .......................................... C07D 251/60
[52] U.S. Cl. .................................................. 544/201
[58] Field of Search ........................................ 544/201

[56] References Cited

U.S. PATENT DOCUMENTS 3,300,493  1/1967  Hamprecht ......................... 544/201
3,895,007  7/1975  Schwarzmann et al. ........... 544/201

FOREIGN PATENT DOCUMENTS 1209570  8/1966  Fed. Rep. of Germany .
54-22385  2/1979  Japan .

*Primary Examiner*—John M. Ford
*Attorney, Agent, or Firm*—Keil & Witherspoon

[57] ABSTRACT

In the synthesis of melamine by conversion of urea in a fluidized catalyst bed, the melamine quality is improved by reactivating the catalyst by treating it, in the fluidized bed, with gases containing steam, in the absence of oxygen, at from 250° to 450° C.

3 Claims, No Drawings

MELAMINE QUALITY BY REACTIVATION OF THE MELAMINE SYNTHESIS CATALYST

The present invention relates to a process for improving the quality of the melamine, obtained by chemical catalytic conversion of urea, through reactivation of the catalyst.

It is known that in the synthesis of melamine from urea, carried out in the presence of a catalyst at from 300° to 450° C. under a pressure of from 1 to 10 bar, in the presence of ammonia or gases containing ammonia, for example a mixture of ammonia and carbon dioxide such as that which is obtained by freeing the reaction gas from melamine and which consists essentially of 2 parts by volume of ammonia and 1 part by volume of carbon dioxide, as a carrier gas, less volatile by-products, such as melem, melamine cyanurate and cyameluric acid, are also formed.

The catalyst pores and surface become increasingly clogged with these non-volatile products, so that in sustained operation the activity of the catalyst decreases progressively, and the gas mixture leaving the reactor contains ever-increasing proportions of isocyanic acid, which, when the reaction gases are cooled to deposit the melamine, reacts with the latter to form melamine cyanurate etc. These impurities in melamine interfere with the production of finishes from melamine-formaldehyde resins. Since they (for example in the case of melamine cyanurate) are present in an insoluble very finely divided form, they can be removed from the melamine-formaldehyde solutions only at great expense, if at all.

It is true that by bringing the pH to an alkaline value, for example by adding sodium hydroxide solution, the organic impurities which are present in the melamine and are insoluble in pure formaldehyde can be brought into solution, but in some recipes for the preparation of melamine-formaldehyde resins it is not possible to employ an alkaline pH.

A catalyst whose activity has dropped can be reactivated by flushing it in a known manner with ammonia at the reaction temperature for a prolonged period (German Pat. No. 1,209,570). It is true that melem can thereby be converted to melamine, but the remaining substances which also reduce the activity of the catalyst cannot be removed completely, and moreover this method entails an economically unacceptable consumption of ammonia.

According to German Pat. No. 1,209,570 this disadvantage can be avoided by carrying out the reaction in two stages and interchanging the catalysts periodically between the first and second stages. However, this procedure is relatively expensive.

According to Japanese Patent Application No. 22,385/79, the catalysts are freed from impurities by bringing them into contact, at from 380° to 800° C., with oxygen, or oxygen-containing gas, which contains steam, thereby burning away the adhering organic substances. This process has the great disadvantage that the oxygen treatment of the catalyst, which may be pyrophoric, has to be carried out under strictly controlled conditions in order to avoid a runaway reaction, ie. an uncontrolled rise in temperature, since at higher temperatures there is a danger of the catalyst being damaged through a change in its lattice structure. A further disadvantage is that the burning off of the impurities cannot be carried out in the reactor itself, since the reactors employed for the synthesis of melamine are not designed for the high temperatures which may arise in such burning off. To carry out this process, the catalyst must therefore be removed from the reactor and treated in a special oven. This means an enormous expense in the case of an industrial plant, and hence the process is also not useful in practice.

It is an object of the present invention to provide a process for improving the quality of melamine by reactivating the catalysts, which have been employed in the synthesis of melamine by thermal conversion of urea in a fluidized catalyst bed, through treatment with gases containing steam, which process can be carried out safely, and without major expense, in industrial operation, reactivation being carried out without removing the catalyst from the synthesis reactor.

We have found that this object is achieved if the catalyst in the fluidized bed is treated with gases which contain steam, in the absence of oxygen, at from 250° to 450° C.

Surprisingly, the treatment of the catalysts, in accordance with the invention, can be carried out during the synthesis of the melamine, ie. the steam or water can be introduced into the reaction zone without interrupting the feed of urea. Though, in this procedure, urea or its conversion products are hydrolyzed, the catalysts resume their original activity. Of course, the treatment according to the invention can also be effected after stopping the urea feed. The novel treatment achieves complete reactivation of the catalyst, ie. immediately after stopping the supply of water or steam, melamine is again produced in the original yield and purity.

The process according to the invention can be carried out by introducing either steam or liquid water into the fluidized bed, since liquid water in any case vaporizes immediately at the temperatures to be maintained in the process according to the invention, namely from 250° to 450° C., preferably from 350° to 450° C. The steam is diluted with the gas used to fluidize the catalyst. In practice, it has proved advantageous to feed into the fluidizied bed an amount of water or steam which is such that the gases have a steam content of from 0.5 to 15% by volume; of course, the reactivation takes place more rapidly at higher steam contents than at lower contents. Equally, higher temperatures within the stated range accelerate the reactivation.

The catalysts employed in the synthesis of melamine are usually oxidic compounds, such as silica gel, aluminum silicates, oxides of titanium, zirconium or thorium, and also kaolin, bentonite, bauxite, diatomaceous earth and fuller's earth, but especially aluminum oxide.

The duration of the treatment according to the invention is from 1 to 24 hours depending on the degree of clogging of the catalyst, the temperature employed and the steam concentration. The required amount of water is preferably introduced into the fluidized bed via the urea injection nozzles, whilst if steam is employed it is advantageously admixed to the fluidizing gas.

The fluidizing gas used in the treatment according to the invention and during the synthesis itself is, in particular, a gas consisting of ammonia and carbon dioxide, expecially the synthesis waste gas, ie. the gas which has been freed from melamine and urea and contains ammonia and carbon dioxide in a volume ratio of about 2:1.

The process according to the invention has the advantage, over the prior processes for regenerating a melamine synthesis catalyst, that the regeneration can be carried out in the synthesis reactor, ie. without removing and reinstalling the catalyst, and that all which is necessary when there is a drop in the catalyst activity, which, as mentioned, can be detected through the quality of the product, is that in place of urea water or steam is introduced into the reactor under otherwise unchanged conditions, or that during the synthesis water or steam is introduced into the reactor.

The Examples which follow illustrate the advantages of the novel process.

EXAMPLE 1

(A) Per hour, 2.1 t of melamine are produced in a fluidized bed reactor, charged with a $\gamma$-$Al_2O_3$ catalyst, by injecting 6 t of molten urea at a reaction temperature of 390° C. The catalyst is fluidized by means of a gas consisting of 70% by volume of ammonia and 30% by volume of carbon dioxide. The vaporous melamine obtained after removing by-products and abraded catalyst is desublimed by supplying cooled reaction gas, and is separated out by means of downstream cyclones and then discharged.

The quality of this melamine is examined by dissolving 63 g of melamine in a mixture of 100 ml of 30% strength by weight formaldehyde and 9 g of distilled water by heating at 90°-95° C., with stirring. The solution is assessed as to whether it is clear, opalescent or cloudy. If it is cloudy or opalescent, the product quality of the melamine is improved by injecting water instead of liquid urea into the reaction zone of the fluidized bed reactor under the above reaction conditions. The amount of water added corresponds, after vaporization, to 5.9% by volume of the fluidizing gas. After 20 hours, the feed of water is stopped and the introduction of urea into the reactor resumed. The melamine formed is again examined. The melamine-formaldehyde solution now proves completely clear and the product quality is maintained for at least 8 weeks.

(B) If the melamine prepared as described in Example 1 does not give a clear solution in formaldehyde unless NaOH solution is added, gaseous ammonia is additionally introduced into the fluidizing gas which normally consists of about 70% by volume of $NH_3$ and about 30% by volume of $CO_2$. The amount of added ammonia is 7.3% by volume of the fluidizing gas, and this additional ammonia is introduced for 48 hours. During this time, the injection of liquid urea into the reactor is stopped. The temperature in the fluidized bed reactor is set to 395° C.

After 48 hours, the reaction temperature of the fluidized bed reactor is returned to 390° C. and the production of melamine from 6 t/h of liquid urea is continued in the normal manner.

The quality of the malamine now produced is examined. The product still does not give a clear solution in formaldehyde.

EXAMPLE 2

If the melamine prepared as in section (A) of Example 1 does not give a clear solution in formaldehyde without addition of NaOH solution, but does so if 1 N NaOH solution is added until the pH is 8-9, the product quality can also be improved more quickly by injecting water for 5 hours into the reaction zone of the fluidized bed reactor, at a reaction temperature of 395° C., the amount of water being so chosen that the steam content of the fluidizing gas is 11.2% by volume. The feed of liquid urea is stopped at the same time. Thereafter, the reaction temperature of the fluidized bed reactor is restored to 390° C. and the production of melamine from liquid urea is continued. The melamine formed is again investigated. It gives a clear solution in formaldehyde without addition of NaOH solution. The product quality is maintained for at least 6 weeks.

EXAMPLE 3

The product quality of the melamine prepared as in Example 2 can also be improved by injecting steam for 24 hours into the reaction zone over the fluidized bed reactor at a reaction temperature of 395° C. and choosing the amount of steam to be such that the fluidizing gas contains 3.8% by volume of steam. In other respects, the procedure of Example 2 is followed. The improved product quality is maintained for about 5 weeks.

EXAMPLE 4

If the melamine prepared in section (A) of Example 1 gives opalescent or cloudy resin solutions with formaldehyde, which clear if the pH of the resin solution is brought to 8-9, the product quality can also be improved, without stopping the feed of 6 t/h of liquid urea to the reactor, by blowing steam into the fluidizing gas, consisting of 70% by volume of $NH_3$ and 30% by volume of $CO_2$, in an amount such that the fluidizing gas contains 0.8% by volume of steam.

If the steam is introduced for 1 hour at a reaction temperature of 395° C., the improved melamine quality is maintained for about 10 days.

We claim:

1. A process for improving the quality of melamine by reactivating the catalysts, which have been employed in the synthesis of melamine by thermal conversion of urea in a fluidized catalyst bed, through treatment with gases containing steam, wherein the catalyst in the fluidized bed is treated with steam-containing gases in the absence of oxygen at from 250° to 450° C.

2. A process as claimed in claim 1, wherein the treatment is carried out at from 350° to 450° C.

3. A process as claimed in claim 1 or 2, wherein the treatment is carried out during the synthesis.

* * * * *